(12) United States Patent
Yamamoto et al.

(10) Patent No.: US 11,559,283 B2
(45) Date of Patent: Jan. 24, 2023

(54) ULTRASOUND DIAGNOSIS APPARATUS AND METHOD OF CONTROLLING ULTRASOUND DIAGNOSIS APPARATUS

(71) Applicant: FUJIFILM Corporation, Tokyo (JP)

(72) Inventors: Hiroaki Yamamoto, Ashigarakami-gun (JP); Tomoki Inoue, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 35 days.

(21) Appl. No.: 16/825,903

(22) Filed: Mar. 20, 2020

(65) Prior Publication Data
US 2020/0214673 A1 Jul. 9, 2020

Related U.S. Application Data

(63) Continuation of application No. PCT/JP2018/028013, filed on Jul. 26, 2018.

(30) Foreign Application Priority Data

Sep. 22, 2017 (JP) .............................. JP2017-182854

(51) Int. Cl.
A61B 8/08 (2006.01)
A61B 8/15 (2006.01)
(Continued)

(52) U.S. Cl.
CPC ................ A61B 8/463 (2013.01); A61B 8/06 (2013.01); A61B 8/0891 (2013.01); A61B 8/15 (2013.01);
(Continued)

(58) Field of Classification Search
CPC ........... A61B 8/06; A61B 8/0891; A61B 8/15; A61B 8/46; A61B 8/463; A61B 8/466;
(Continued)

(56) References Cited

U.S. PATENT DOCUMENTS

2003/0092991 A1   5/2003 Sehgal
2003/0229285 A1   12/2003 Simpson et al.
(Continued)

FOREIGN PATENT DOCUMENTS

JP    2006-141798 A    6/2006
JP    2010-94220 A     4/2010
(Continued)

OTHER PUBLICATIONS

Extended European Search Report for European Application No. 18858868.5, dated Oct. 20, 2020.
(Continued)

Primary Examiner — Yi-Shan Yang
Assistant Examiner — Alexei Bykhovski
(74) Attorney, Agent, or Firm — Birch, Stewart, Kolasch & Birch, LLP

(57) ABSTRACT

An ultrasound diagnosis apparatus including: an ultrasound probe having a transducer array; and a processor configured to: perform transmission and reception of an ultrasonic beam from the transducer array toward a subject, into which contrast media including microbubbles is introduced; image a reception signal output from the transducer array to generate an ultrasound image of the subject; acquire trajectories of the microbubbles in a one cross section of the subject by tracking movement of the microbubbles based on the ultrasound image corresponding to the one cross section of the subject; detect, as a feature point, a trajectory, in which a distance between a start point and an end point in a prescribed time range is less than a prescribed value, among the trajectories of the microbubbles; and display the ultrasound image, the acquired trajectories and the detected feature point on the display unit.

19 Claims, 9 Drawing Sheets

(51) Int. Cl.
*A61B 8/00* (2006.01)
*A61B 8/06* (2006.01)

(52) U.S. Cl.
CPC .............. *A61B 8/481* (2013.01); *A61B 8/483* (2013.01); *A61B 8/56* (2013.01)

(58) Field of Classification Search
CPC ....... A61B 8/481; A61B 8/483; A61B 8/5223; A61B 8/56; G01S 15/8915; G01S 15/8993; G01S 7/52039; G01S 7/52073; G01S 7/52074
See application file for complete search history.

(56) References Cited

U.S. PATENT DOCUMENTS

| | | | |
|---|---|---|---|
| 2006/0116582 A1 | 6/2006 | Yoshida | |
| 2008/0269611 A1* | 10/2008 | Pedrizzetti | A61B 8/06 600/454 |
| 2010/0094133 A1 | 4/2010 | Yoshiara et al. | |
| 2013/0345566 A1* | 12/2013 | Weitzel | A61B 8/488 600/445 |
| 2014/0276062 A1* | 9/2014 | Kondoh | A61B 8/5207 600/443 |
| 2016/0119529 A1* | 4/2016 | Stolka | G06F 9/453 348/211.1 |
| 2017/0164923 A1* | 6/2017 | Matsumoto | A61B 8/4416 |
| 2020/0234446 A1* | 7/2020 | Mischi | G16H 50/30 |

FOREIGN PATENT DOCUMENTS

| | | |
|---|---|---|
| JP | 2011-189175 A | 9/2011 |
| WO | WO 2017/042280 A1 | 3/2017 |

OTHER PUBLICATIONS van Sloun et al., "Ultrasound-contrast-agent dispersion and velocity imaging for prostate cancer localizaton," Medical Image Analysis, vol. 35, 2017 (published online Oct. 1, 2016) pp. 610-619.
International Preliminary Report on Patentability and English translation of the Written Opinion of the International Searching Authority (Forms PCT/IB/326, PCT/IB/373, and PCT/ISA/237) for International Application No. PCT/JP2018/028013, dated Apr. 2, 2020.
International Search Report (Form PCT/ISA/210) for International Application No. PCT/JP2018/028013, dated Sep. 18, 2018, with English translation.

* cited by examiner

ULTRASOUND DIAGNOSIS APPARATUS AND METHOD OF CONTROLLING ULTRASOUND DIAGNOSIS APPARATUS

CROSS-REFERENCE TO RELATED APPLICATIONS

This application is a Continuation of PCT International Application No. PCT/JP2018/028013 filed on Jul. 26, 2018, which claims priority under 35 U.S.C § 119(a) to Japanese Patent Application No. 2017-182854 filed on Sep. 22, 2017. Each of the above applications is hereby expressly incorporated by reference, in its entirety, into the present application.

BACKGROUND OF THE INVENTION

1. Field of the Invention

The present invention relates to an ultrasound diagnosis apparatus and a method of controlling an ultrasound diagnosis apparatus, and in particular, to an ultrasound diagnosis apparatus that images a part of a subject, into which contrast media is introduced, and a method of controlling an ultrasound diagnosis apparatus.

2. Description of the Related Art

Heretofore, an ultrasound diagnosis apparatus is known as an apparatus that obtains an image of the inside of a subject. In general, the ultrasound diagnosis apparatus transmits an ultrasonic beam from a transducer array, in which a plurality of elements are arranged, toward the inside of the subject and receives an ultrasonic echo from the subject in the transducer array to acquire element data. In addition, the ultrasound diagnosis apparatus electrically processes the acquired element data, thereby being able to generate an ultrasound image in which a part of the subject is reflected.

In this way, in generating the ultrasound image of the subject using the ultrasound diagnosis apparatus, there is a case where an ultrasonic beam is transmitted to the subject, into which contrast media including microbubbles is introduced, and an ultrasonic echo from the subject is received to generate an ultrasound image. In this case, the microbubbles of the contrast media introduced into the subject show a nonlinear response accompanied with deformation or destruction due to the ultrasonic beam transmitted from the transducer array of the ultrasound diagnosis apparatus. In this case, in a case where a frequency of the transmitted ultrasonic beam is referred to as f, a harmonic signal, such as 2f or 3f, is included in a response signal to the microbubbles. On the other hand, a reflection signal from a tissue other than the microbubbles is included in the ultrasonic echo received in the transducer array, and a harmonic signal caused by a nonlinear response of the tissue is also included in the reflection signal from such a tissue. However, since a generation rate of the harmonic signal from the microbubble is significantly higher than a generation rate of the harmonic signal from the tissue, as a band of the harmonic signal in the ultrasonic echo received in the transducer array is imaged, it is possible to obtain an ultrasound image in which a spot where contrast media is introduced is clearly reflected. Since a user often diagnoses the part or the like of the subject based on such as ultrasound image, various improvements have been made in the ultrasound diagnosis apparatus such that the user can perform accurate diagnosis.

For example, JP2006-141798A discloses an ultrasound diagnosis apparatus that transmits a high-power ultrasonic pulse causing destruction of microbubbles toward a subject, into which the contrast media is introduced, at a timing instructed by a user while transmitting a low-power ultrasonic pulse not causing destruction of the microbubbles included in contrast media toward the subject. The ultrasound diagnosis apparatus disclosed in JP2006-141798A tracks microbubbles that are partially destroyed and separated by the high-power ultrasonic pulse and become a small mass, thereby being able to obtain an ultrasound image that reflects the speed and amount of microbubbles flowing in individual blood vessels.

Furthermore, JP2010-94220A discloses an ultrasound diagnosis apparatus that sets a plurality of regions in an ultrasound image generated for a subject, into which contrast media is introduced, and tracks microbubbles included in the contrast media based on signal intensity in a plurality of set regions. The ultrasound diagnosis apparatus disclosed in JP2010-94220A calculates a relative time at which the contrast media flows into each region with one region as a reference and display each region in a different color according to the calculated relative time, thereby being able to present the relative inflow time of the contrast media among a plurality of regions in an easily visible manner.

SUMMARY OF THE INVENTION

Meanwhile, in JP2006-141798A and JP2010-94220A, in regards to a blood vessel extended along a cross section of the generated ultrasound image, the microbubbles of the contrast media introduced into the blood vessel can be tracked; however, a blood vessel extended along a direction penetrating the cross section of the generated ultrasound image vertically or in an inclined manner is not taken into consideration. For this reason, the ultrasound diagnosis apparatus disclosed in JP2006-141798A and JP2010-94220A shows information obtained from an ultrasound image corresponding to only one cross section to the user, and the user performs diagnosis based on such information. As a result, there is a concern that the diagnosis accuracy of the user is degraded.

The invention has been accomplished in order to solve such a problem in the related art, and an object of the invention is to provide an ultrasound diagnosis apparatus and a method of controlling an ultrasound diagnosis apparatus capable of improving diagnosis accuracy of a user for a subject.

In order to achieve the above-described object, the invention provides an ultrasound diagnosis apparatus comprising an ultrasound probe having a transducer array, an imaging unit that performs transmission and reception of an ultrasonic beam from the transducer array toward a subject, into which contrast media including microbubbles is introduced, and generates an ultrasound image of the subject from a reception signal outputted by the transducer array, a bubble tracking unit that tracks movement of the microbubbles based on the ultrasound image generated by the imaging unit corresponding to one cross section to acquire trajectories of the microbubbles in the one cross section and displays the acquired trajectories on the display unit, and a feature point detection unit that detects, as a feature point, a trajectory, in which a distance between a start point and an end point in a prescribed time range is less than a prescribed value, among the trajectories of the microbubbles acquired by the bubble tracking unit and displays the detected feature point on the display unit.

It is preferable that the ultrasound diagnosis apparatus further comprises a message creation unit that creates a message for a user such that one or more ultrasound images corresponding to one or more cross sections different from the one cross section are obtained in a case where the one or more feature points are detected by the feature point detection unit. It is preferable that the one or more different cross sections are cross sections that are inclined with respect to the one cross section and passes through the feature point. In this case, it is preferable that, in a case where a plurality of the feature points is detected by the feature point detection unit, the message creation unit creates a message for a user such that ultrasound images corresponding to a plurality of the cross sections passing through the respective feature points are obtained.

The different cross sections may be a plurality of cross sections parallel to the one cross section. It is preferable that the message creation unit creates the message instructing the user to move a position of the ultrasound probe and generate the ultrasound image using the imaging unit.

The different cross section may be a plurality of cross sections having inclination angles different from one another with respect to the one cross section. It is preferable that the ultrasound probe is a probe that is able to perform scanning with the ultrasonic beam from the transducer array in a three-dimensional manner. It is preferable that the message creation unit creates the message instructing the user to perform transmission and reception of an ultrasonic beam along scanning planes having inclination angles different from one another while fixing a position of the ultrasound probe, and generate the ultrasound image using the imaging unit.

It is preferable that the bubble tracking unit tracks movement of the microbubbles in the one or more different cross sections based on the one or more ultrasound images generated for the one or more different cross sections to acquire the trajectories of the microbubbles and displays the acquired trajectories on the display unit.

It is preferable that the contrast media is introduced into a blood vessel of the subject, and the ultrasound diagnosis apparatus further comprises a blood vessel image creation unit that creates a blood vessel image of the subject based on the trajectories of the microbubbles acquired by the bubble tracking unit. In this case, it is preferable that the ultrasound diagnosis apparatus further comprises a blood vessel information acquisition unit that acquires blood vessel information of the subject from the blood vessel image created by the blood vessel image creation unit. It is preferable that the blood vessel information is at least one of a shape of the blood vessel, a thickness of the blood vessel, the number of blood vessels, or a flow velocity of blood.

It is preferable that the ultrasound diagnosis apparatus further comprises a diagnosis unit that performs diagnosis of the subject based on the blood vessel information acquired by the blood vessel information acquisition unit. It is preferable that the feature point detection unit performs at least one of changing of color of the detected feature point or marking on the feature point to make the display unit highlight the feature point.

The invention also provides a method of controlling an ultrasound diagnosis apparatus. The method comprises performing transmission and reception of an ultrasonic beam toward a subject, into which contrast media including microbubbles is introduced, and generating an ultrasound image of the subject from imaging a reception signal to be output, displaying the generated ultrasound image, tracking movement of the microbubbles based on the ultrasound image generated corresponding to one cross section to acquire trajectories of the microbubbles in the one cross section and displaying the acquired trajectories, and detecting, as a feature point, a trajectory, in which a distance between a start point and an end point in a prescribed time range is less than a prescribed value, among the trajectories of the microbubbles and displaying the detected feature point.

According to the invention, since the ultrasound diagnosis apparatus comprises the feature point detection unit that detects, as the feature point, the trajectory, in which the distance between the start point and the end point in the prescribed time range is less than the prescribed value, among the trajectories of the microbubbles acquired by the bubble tracking unit and displays the detected feature point on the display unit, it is possible to improve the diagnosis accuracy of the user for the subject.

DESCRIPTION OF THE PREFERRED EMBODIMENTS

Hereinafter, an embodiment of the invention will be described referring to the accompanying drawings.

Embodiment 1

Figure 1:
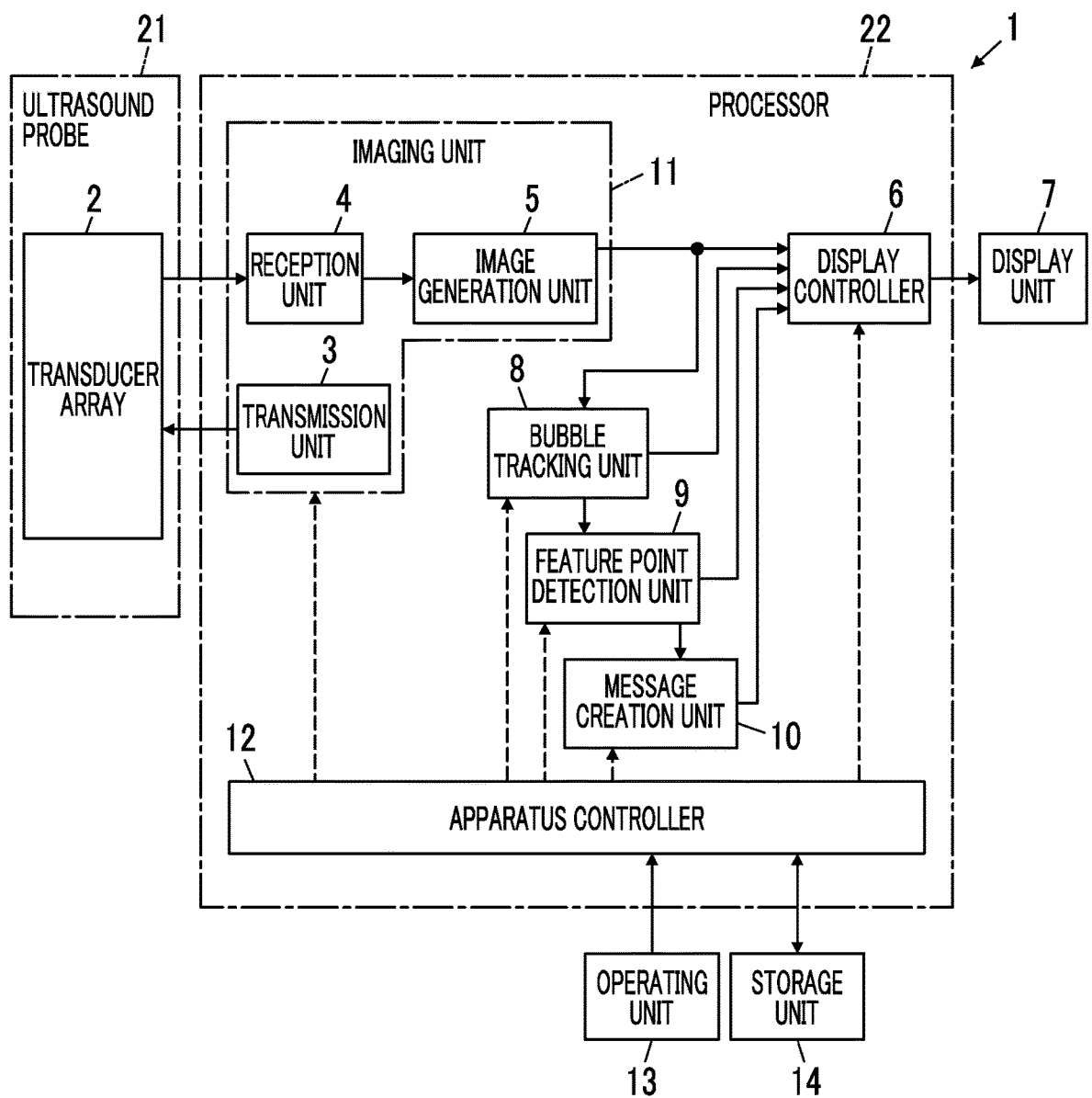
FIG. 1 is a block diagram showing the configuration of an ultrasound diagnosis apparatus according to Embodiment 1 of the invention.

FIG. 1 shows the configuration of an ultrasound diagnosis apparatus 1 according to Embodiment 1 of the invention. As shown in FIG. 1, the ultrasound diagnosis apparatus 1 comprises a transducer array 2, and a transmission unit 3 and a reception unit 4 are connected to the transducer array 2. An image generation unit 5, a display controller 6, and a display unit 7 are sequentially connected to the reception unit 4. A bubble tracking unit 8 is connected to the image generation unit 5, a feature point detection unit 9 is connected to the bubble tracking unit 8, and a message creation unit 10 is connected to the feature point detection unit 9. The bubble tracking unit 8, the feature point detection unit 9, and the message creation unit 10 are connected to the display controller 6. Here, the transmission unit 3, the reception unit 4, and the image generation unit 5 constitute an imaging unit 11. In addition, an apparatus controller 12 is connected to the display controller 6, the bubble tracking unit 8, the feature point detection unit 9, the message creation unit 10, and the imaging unit 11, and an operating unit 13 and a storage unit 14 are connected to the apparatus controller 12.

Furthermore, the transducer array 2 is included in an ultrasound probe 21, and the display controller 6, the bubble tracking unit 8, the feature point detection unit 9, the message creation unit 10, and the imaging unit 11 constitute a processor 22.

The transducer array 2 of the ultrasound probe 21 shown in FIG. 1 has a plurality of elements (ultrasound transducers) arranged in a one-dimensional or two-dimensional manner. Each element transmits an ultrasonic wave in response to an actuation signal supplied from the transmission unit 3, receives a reflected wave from a subject, and outputs a reception signal. Each element is constituted of a transducer in which electrodes are formed at both ends of a piezoelectric body made of, for example, piezoelectric ceramic represented by lead zirconate titanate (PZT), a polymer piezoelectric element represented by poly vinylidene di fluoride (PVDF), piezoelectric single crystal represented by a lead magnesium niobate-lead titanate (PMN-PT), or the like.

The transmission unit 3 of the imaging unit 11 includes, for example, a plurality of pulse generators, and adjusts an delay amount of each actuation signal based on a transmission delay pattern selected in response to a control signal from the apparatus controller 12 such that ultrasonic waves transmitted from a plurality of elements of the transducer array 2 form an ultrasonic beam and supplies the actuation signals to a plurality of elements. In this way, in a case where a pulsed or continuous-wave voltage is applied to the electrodes of each of the elements of the transducer array 2, the piezoelectric body expands and contracts to generate pulsed or continuous-wave ultrasonic waves from the respective transducers. An ultrasonic beam is formed from a combined wave of the ultrasonic waves.

The transmitted ultrasonic beam is reflected by, for example, a target, such as a part of the subject, and propagates toward the transducer array 2 of the ultrasound probe 21. The ultrasonic waves propagating toward the transducer array 2 in this way are received by the respective elements constituting the transducer array 2. In this case, the respective transducers constituting the transducer array 2 expand and contract with reception of the propagating ultrasonic waves to generate electrical signals. The electrical signals are output from the respective elements to the reception unit 4 as reception signals of the ultrasonic waves.

Figure 2:
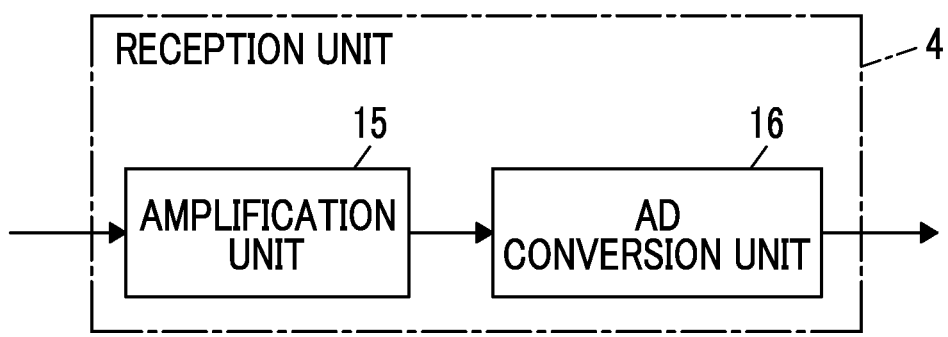
FIG. 2 is a block diagram showing the internal configuration of a reception unit in Embodiment 1 of the invention.

As shown in FIG. 2, the reception unit 4 of the imaging unit 11 has a configuration in which an amplification unit 15 and an analog digital (AD) conversion unit 16 are connected in series. The amplification unit 15 amplifies the reception signals of the ultrasonic waves input from the respective elements constituting the transducer array 2 and transmits the amplified reception signals to the AD conversion unit 16. The AD conversion unit 16 converts the reception signals transmitted from the amplification unit 15 to digital element data and outputs the element data to the image generation unit 5.

Figure 3:
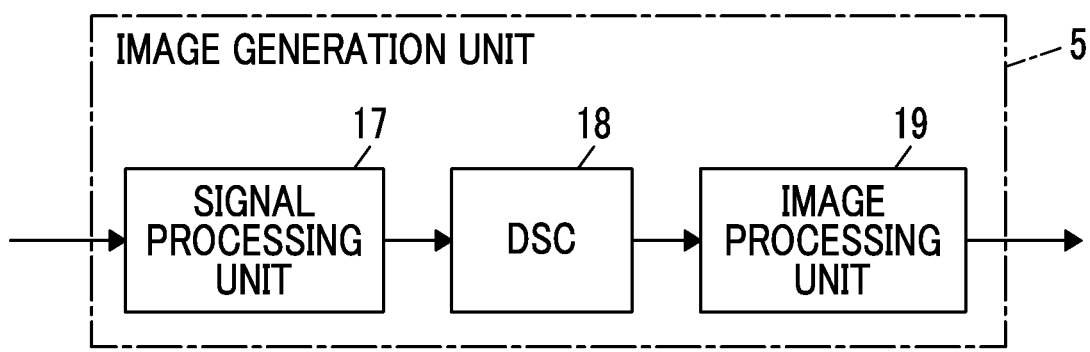
FIG. 3 is a block diagram showing the internal configuration of an image generation unit in Embodiment 1 of the invention.
Figure 4:
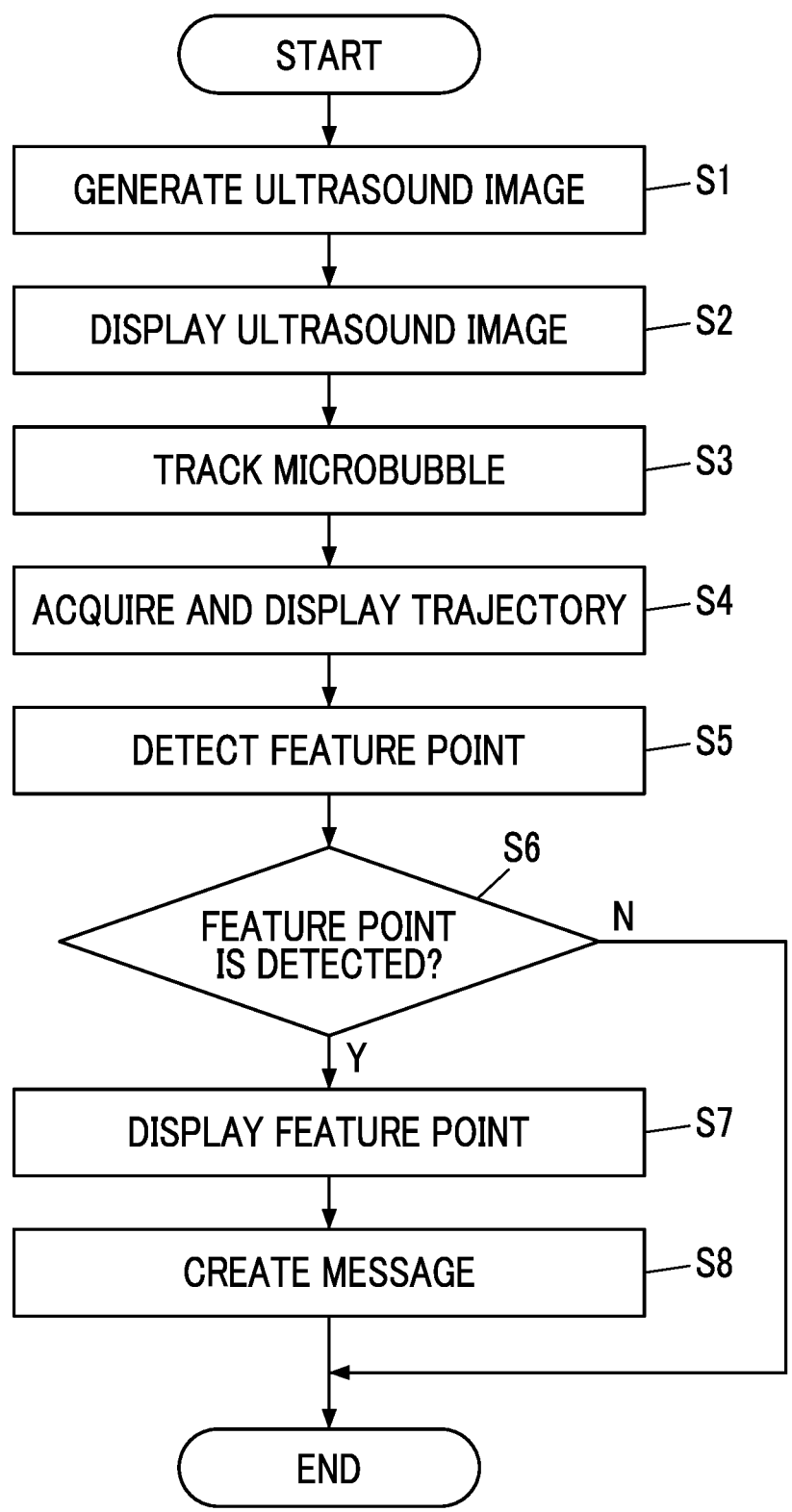
FIG. 4 is a flowchart showing an operation of the ultrasound diagnosis apparatus in Embodiment 1 of the invention.

As shown in FIG. 3, the image generation unit 5 of the processor 22 has a configuration in which a signal processing unit 17, a digital scan converter (DSC) 18, and an image processing unit 19 are connected in series. The signal processing unit 17 executes reception focus processing in which a delay is given to each piece of element data according to a set sound speed and addition (phasing addition) is performed based on a reception delay pattern selected in response to a control signal from the apparatus controller 12. Through the reception focus processing, a sound ray signal with narrowed focus of the ultrasonic echo is generated. The signal processing unit 17 performs correction of attenuation due to a propagation distance on the generated sound ray signal according to a depth of a reflection position of the ultrasonic wave, and then, executes envelope detection processing, thereby generating a B mode image signal that is tomographic image information relating to a tissue inside the subject. The B mode image signal generated in this way is output to the DSC 18.

The DSC 18 raster-converts the B mode image signal to an image signal according to a normal television signal scanning system. The image processing unit 19 executes various kinds of needed image processing, such as brightness correction, gradation correction, sharpness correction, and color correction, on image data obtained in the DSC 18 and outputs the B mode image signal to the display controller 6. In the following description, the B mode image signal is referred to as an ultrasound image.

In a case where, in a case where ultrasound images of a plurality of frames are generated by the image generation unit 5 for the subject, into which contrast media including microbubbles is introduced, the bubble tracking unit 8 of the processor 22 tracks movement of the microbubbles based on the ultrasound image generated by the image generation unit 5 corresponding to one cross section, acquires trajectories of the microbubbles in one cross section, and displays the acquired trajectories on the display unit 7 through the display controller 6. As a specific tracking method of the microbubbles, for example, the bubble tracking unit 8 can track the microbubbles by dividing the ultrasound images of a plurality of frames generated by the image generation unit 5 into a plurality of regions and performing so-called block matching for each divided region.

The bubble tracking unit 8 holds, as information relating to the movement of the tracked microbubble, a tracking time to the microbubble in conjunction with the acquired trajectory. For example, the bubble tracking unit 8 can hold an elapsed time from the start to the end of the tracking of the microbubble or can hold a time for which the microbubble is being tracked. In this case, for example, the bubble tracking unit 8 can apply a gradation of color corresponding to the tracking time of the microbubble to the acquired trajectory and can display the colored trajectory on the display unit 7. With this, it is possible to allow the user to visually and simply ascertain the tracking time to the microbubble.

The feature point detection unit 9 of the processor 22 detects a feature point based on the trajectory of the microbubble acquired by the bubble tracking unit 8 and displays the detected feature point on the display unit 7 through the display controller 6. In this case, the feature point detection unit 9 can detect, as the feature point, a trajectory, in which a distance between a start point and an end point in a prescribed time range is less than a prescribed value, among the trajectories of the microbubbles acquired by the bubble tracking unit 8.

Specifically, for example, the feature point detection unit 9 can set a total time from the start to the end of the tracking of the microbubble in the bubble tracking unit 8 as the prescribed time range, and can detect, as a feature point, a trajectory, in which a distance between a position (start point) of the microbubble at the time of the start of the tracking and a position (end point) of the microbubble at the time of the end of the tracking is less than a prescribed value. Alternatively, in a case where the trajectory of the microbubble for the total time from the start to the end of the tracking of the microbubble in the bubble tracking unit 8 is included in a circle having a given radius as a whole, the feature point detection unit 9 may determine that the distance between the start point and the end point is less than the prescribed value and may detect the trajectory as the feature point. As the prescribed value, for example, an average value of a diameter of a human blood vessel or the average value of the diameter of the human blood vessel corresponding to an input measurement spot stored in advance in the ultrasound diagnosis apparatus 1 can be used. The user may input an appropriate value as the prescribed value. Alternatively, the prescribed value may be decided based on a pixel distance of an image under observation. Specifically, in a case where a screen size of the display unit 7 is W 960×H 640, 96 pixels of one tenth of W can be set to a reference of the prescribed value. In a case where the screen is zoomed, the reference is magnified. In a case where the ultrasound diagnosis apparatus 1 is of a mobile type, and the user changes the display unit 7 to a vertical placement, 64 pixels of one tenth of H can be set to the reference of the prescribed value.

Specifically, for example, the feature point detection unit 9 can set a given time included between the tracking start time and the tracking end time of the microbubble in the bubble tracking unit 8 as the prescribed time range, and can detect, as a feature point, a trajectory, in which the distance between a position (start point) of the microbubble at the start of the given time and a position (end point) of the microbubble at the end of the given time is less than the prescribed value. Alternatively, the feature point detection unit 9 may determine the distance between the start point and the end point for the given time is less than the prescribed value in a case where the trajectory of the microbubble for the given time included between the tracking start time and the tracking end time of the microbubble in the bubble tracking unit 8 is included in the circle having the given radius as a whole, and may detect the trajectory as a feature point.

For example, the feature point detection unit 9 can store a template of a pattern to be detected as a feature point and templates other than the feature point in advance. In this case, the feature point detection unit 9 may detect a feature point through so-called template matching for calculating similarity of the templates stored in advance to the trajectory of the microbubble acquired by the bubble tracking unit 8.

In a case where the feature point is detected by the feature point detection unit 9, the message creation unit 10 of the processor 22 creates a message for instructing the user such that an ultrasound image corresponding to a cross section different from one cross section corresponding to the ultrasound image, in which the feature point is detected. The message creation unit 10 can create, as a message for the user, at least one text data, image data, voice data, or the like.

For example, in a case where the message is text data, image data, or the like, the message creation unit 10 displays the created message on the display unit 7 through the display controller 6. For example, in a case where the message is voice data, the message for the user is emitted as voice.

The apparatus controller 12 of the processor 22 controls the units of the ultrasound diagnosis apparatus 1 based on a program stored in advance in the storage unit 14 or the like and a user's operation through the operating unit 13. The display controller 6 of the processor 22 generates a composite image including at least one of the ultrasound image generated by the image generation unit 5, the trajectory of the microbubble acquired by the bubble tracking unit 8, the feature point detected by the feature point detection unit 9, or the message created by the message creation unit 10 and makes the display unit 7 display the generated composite image.

The display unit 7 of the ultrasound diagnosis apparatus 1 displays the composite image generated by the display controller 6 under the control of the apparatus controller 12, and includes, for example, a display device, such as a liquid crystal display (LCD). The operating unit 13 of the ultrasound diagnosis apparatus 1 is provided for the user performing an input operation, and can comprise a keyboard, a mouse, a trackball, a touch pad, a touch panel, and the like.

The storage unit 14 stores an operation program and the like of the ultrasound diagnosis apparatus 1, and a recording medium, such as a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), a server, or the like can be used.

The display controller 6, the bubble tracking unit 8, the feature point detection unit 9, the message creation unit 10, the imaging unit 11, and the apparatus controller 12 are constituted of a central processing unit (CPU) and a control program causing the CPU to execute various kinds of processing; however, the units may be constituted using digital circuits. The display controller 6, the bubble tracking unit 8, the feature point detection unit 9, the message creation unit 10, the imaging unit 11, and the apparatus controller 12 may be incorporated partially or entirely in one CPU.

Next, an operation of the ultrasound diagnosis apparatus 1 of the invention will be described in detail referring to a flowchart shown in FIG. 4 and FIGS. 5 to 7. First, in Step S1, the image generation unit 5 generates ultrasound images of a plurality of frames corresponding to one cross section. Here, as a premise, it is assumed that the image generation unit 5 generates an ultrasound image for the subject, into which contrast media including microbubbles is introduced. Furthermore, it is assumed that contrast media is introduced into a blood vessel of the subject.

In subsequent Step S2, the display controller 6 displays the ultrasound images generated in Step S1 on the display unit 7. In this case, the display controller 6 may display an ultrasound image of one frame of a plurality of ultrasound images generated in Step S1 on the display unit 7, or may sequentially display the ultrasound images of a plurality of frames generated in Step S1 on the display unit 7. In the following description, for description, it is assumed that the display controller 6 displays the ultrasound image of one frame initially acquired in Step S1 on the display unit 7.

In Step S3, the bubble tracking unit 8 tracks microbubbles that are reflected in the ultrasound images of a plurality of frames generated in Step S1. In subsequent Step S4, the bubble tracking unit 8 acquires the trajectories of the tracked microbubbles and displays the acquired trajectories of the microbubbles on the display unit 7. In this case, for example, the bubble tracking unit 8 displays the acquired trajectories of the microbubbles on the display unit 7 through the display controller 6 so as to be superimposed on the ultrasound image of one frame displayed on the display unit 7 in Step S2. Here, since the contrast media is introduced into the blood vessel of the subject, the trajectories of the microbubbles acquired and displayed in Step S3 coincide with the shape of the blood vessel of the subject.

In subsequent Step S5, the feature point detection unit 9 detects a feature point based on the trajectory of the microbubble acquired in Step S4. For example, the feature point detection unit 9 detects, as a feature point, a trajectory, in which the distance between the start point and the end point in a given time range is less than a prescribed value, among the trajectories of the microbubbles acquired in Step S4. The feature point detected in this way has an independent point shape by the microbubble passing through the blood vessel that penetrates one cross section corresponding to the ultrasound image generated in Step S1 vertically or an inclined manner.

In Step S6, the apparatus controller 12 determines whether or not the feature point is detected in Step S5. Here, in a case where the apparatus controller 12 determines that the feature point is not detected, the operation of the ultrasound diagnosis apparatus 1 ends.

On the other hand, in a case where the apparatus controller 12 determines that the feature point is detected, the process progresses to Step S7, and the feature point detected by the feature point detection unit 9 is displayed on the display unit 7 through the display controller 6. In this case, for example, the feature point detection unit 9 can highlight and display the feature point by changing the color of a spot detected as the feature point, marking the spot detected as the feature point, or the like among the trajectories of the microbubbles displayed on the display unit 7 in Step S4.

In Step S8 subsequent to Step S7, the message creation unit 10 creates a message for the user such that an ultrasound image corresponding to a cross section different from one cross section corresponding to the ultrasound image generated in Step S1 is obtained, and the operation of the ultrasound diagnosis apparatus 1 ends.

Figure 5:
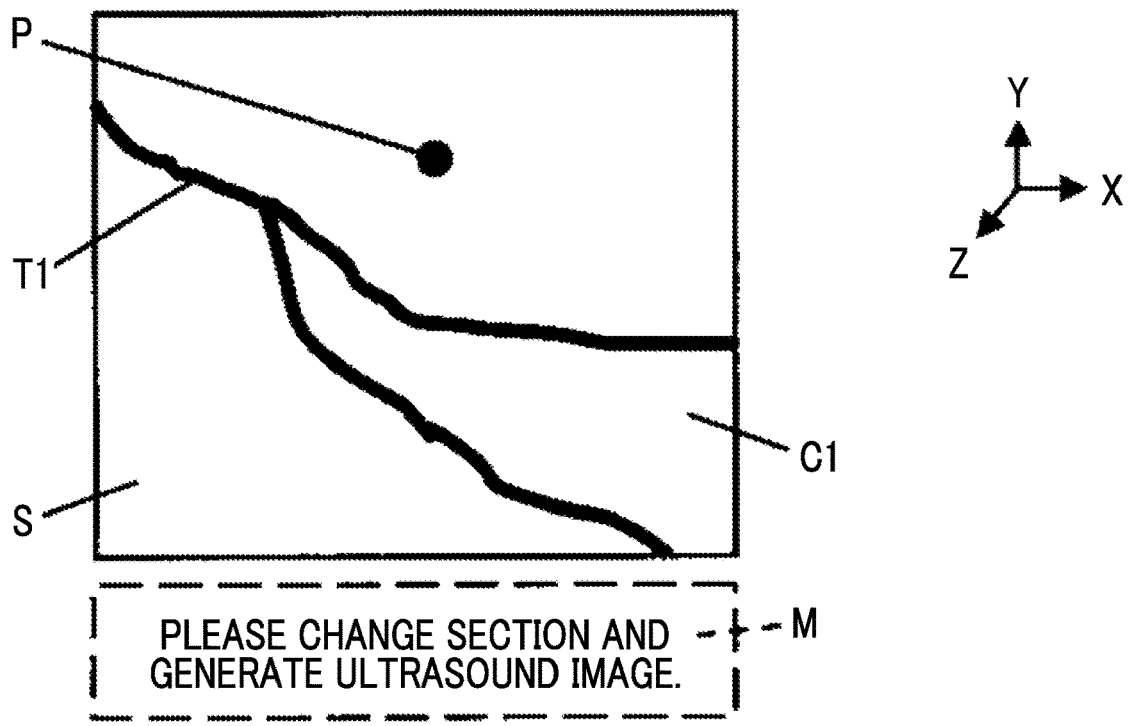
FIG. 5 is a display example of a message for a detected feature point in Embodiment 1 of the invention.

In this case, for example, as shown in FIG. 5, the message creation unit 10 can display a message M for instructing the user to generate the ultrasound image corresponding to the different cross section on the display unit 7 along with the ultrasound image S corresponding to one cross section C1. In the example shown in FIG. 5, a trajectory T1 and a microbubble and a feature point P are displayed in such a manner as to be superimposed on the ultrasound image S. Here, for description, a plane in which one cross section C1 corresponding to the ultrasound image S extends is referred to as an XY plane, and a direction perpendicular to the XY plane is referred to as a Z direction.

Here, the feature point P is highly likely to correspond to a cross section of a blood vessel extending along a direction of penetrating one cross section C1 vertically or in an inclined manner. For this reason, for example, in order to obtain a longitudinal cross section of the blood vessel penetrating the cross section C1 at a position corresponding to the feature point P, it is preferable that a cross section C2 that is inclined with respect to one cross section corresponding to the ultrasound image S and passes through the feature point P is employed as a cross section different from the cross section C1. For this reason, for example, the message creation unit 10 can create a message for instructing the user to generate an ultrasound image while deflecting the direction of the ultrasound probe 21 at 90 degrees and can display the created message on the display unit 7.

Figure 6:
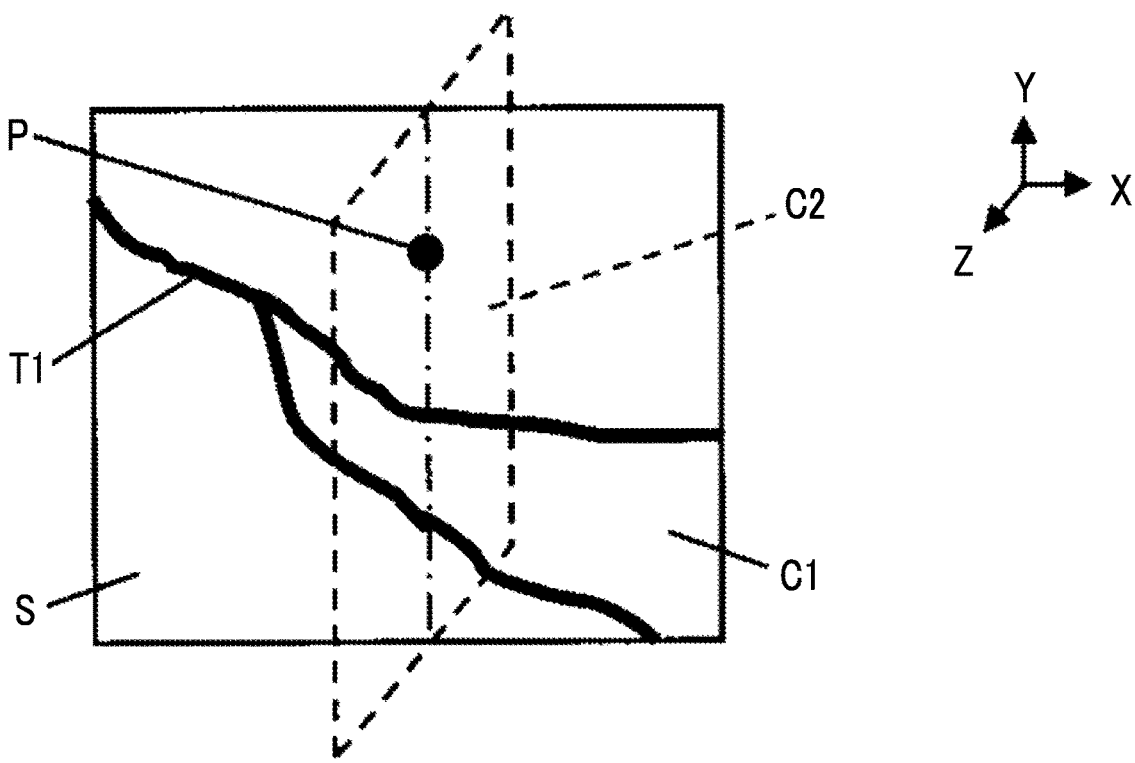
FIG. 6 is a diagram showing a different cross section passing through the detected feature point in Embodiment 1 of the invention.
Figure 7:
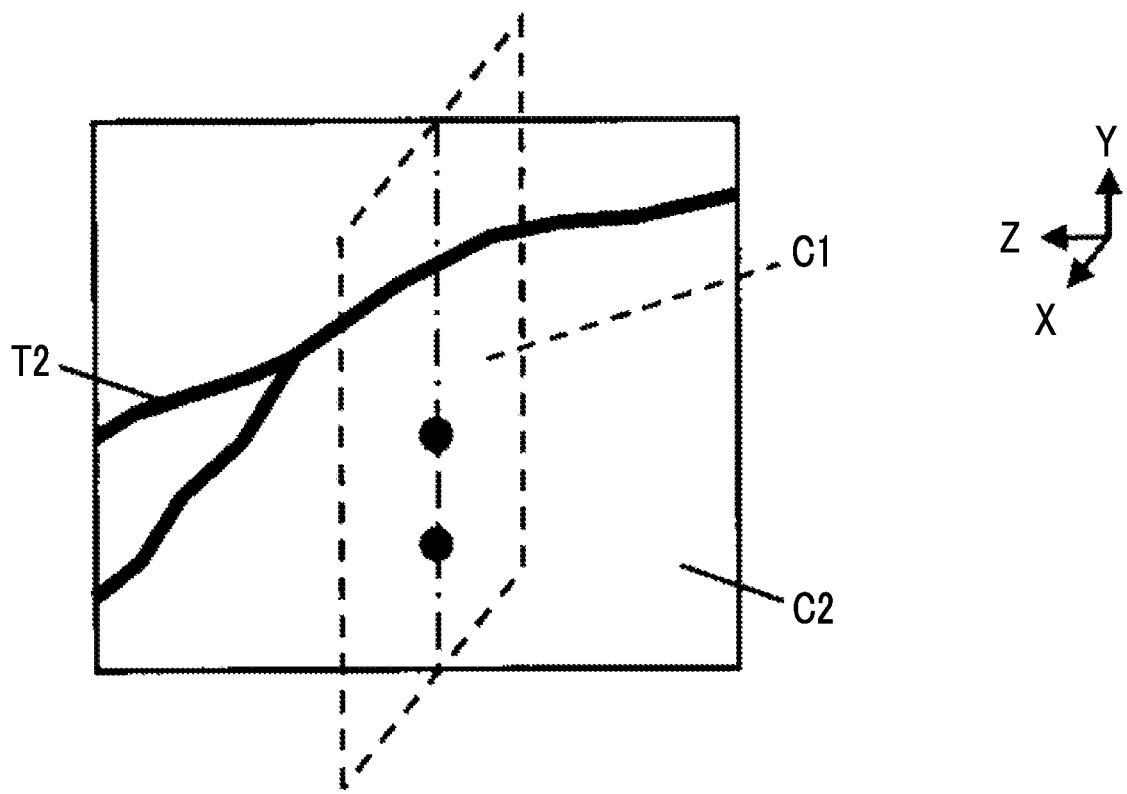
FIG. 7 is a diagram showing an example of an ultrasound image corresponding to the different cross section passing through the detected feature point in Embodiment 1 of the invention.

With this, the user confirms the feature point P and the message M displayed on the display unit 7, and as shown in FIG. 6, changes a position and a direction of the ultrasound probe 21 in order to generate the ultrasound image corresponding to the cross section C2 different from one cross section C1 parallel to the XY plane. In the example shown in FIG. 6, the different cross section C2 is a plane that is parallel to an YZ plane and passes through the feature point P in one cross section C1. As a result, as shown in FIG. 7, the user can obtain a trajectory T2 of the microbubble corresponding to the blood vessel passing through the feature point P in one cross section C1.

As described above, with the ultrasound diagnosis apparatus 1 of the invention, the trajectory of the microbubble of the contrast media introduced into the subject is acquired based on the ultrasound image generated by the image generation unit 5, the feature point is detected from the acquired trajectory, and the detected feature point is displayed on the display unit 7. Thus, it is possible to allow the user to view a post displayed as a feature point, and to prompt the user to generate an ultrasound image corresponding to a cross section different from one cross section, in which the feature point is detected. For this reason, it is possible to allow the user to easily perform diagnosis of a part of the subject based on both of the ultrasound image corresponding to one cross section, in which the feature point is detected, and the ultrasound image newly generated corresponding to the different cross section. As a result, it is possible to improve the diagnosis accuracy of the user for the subject. The message creation unit 10 creates the message for the user corresponding to the detected feature point. Thus, it is possible to more effectively prompt the user to generate the ultrasound image corresponding to the cross section different from one cross section, in which the feature point is detected.

In Step S2, although the ultrasound image is displayed on the display unit 7, in the invention, the ultrasound image is not necessarily displayed on the display unit 7 as long as the acquisition of the trajectory of the microbubble, the display of the trajectory of the microbubble, the detection of the feature point, and the display of the feature point can be performed. For this reason, Step S2 can be omitted. In this case, for example, the ultrasound image may be initially displayed along with the trajectory of the microbubble in Step S4.

In Step S3, although the bubble tracking unit 8 tracks the microbubble based on the ultrasound image corresponding to one cross section, a trigger for starting the tracking of the microbubble and a trigger for ending the tracking of the microbubble can be set, respectively. For example, the generation of the initial ultrasound image in Step S1 can be set as the trigger for starting the tracking of the microbubble. Alternatively, for example, a tracking start button (not shown) for starting the tracking of the microbubble may be displayed on the display unit 7, and the user pressing the tracking start button through the operating unit 13 may be set as the trigger for starting the tracking of the microbubble.

For example, the acquisition of the trajectory of the microbubble having a prescribed distance in Step S3 can be set as the trigger for ending the tracking of the microbubble. Alternatively, for example, the lapse of a prescribed time after the start of the tracking of the microbubble may be set as the trigger for ending the tracking of the microbubble.

Furthermore, for example, a tracking end button (not shown) for ending the tracking of the microbubble may be displayed on the display unit 7, and a press of the tracking end button by the user through the operating unit 13 may be set as the trigger for ending the tracking of the microbubble.

Embodiment 2

Figure 8:
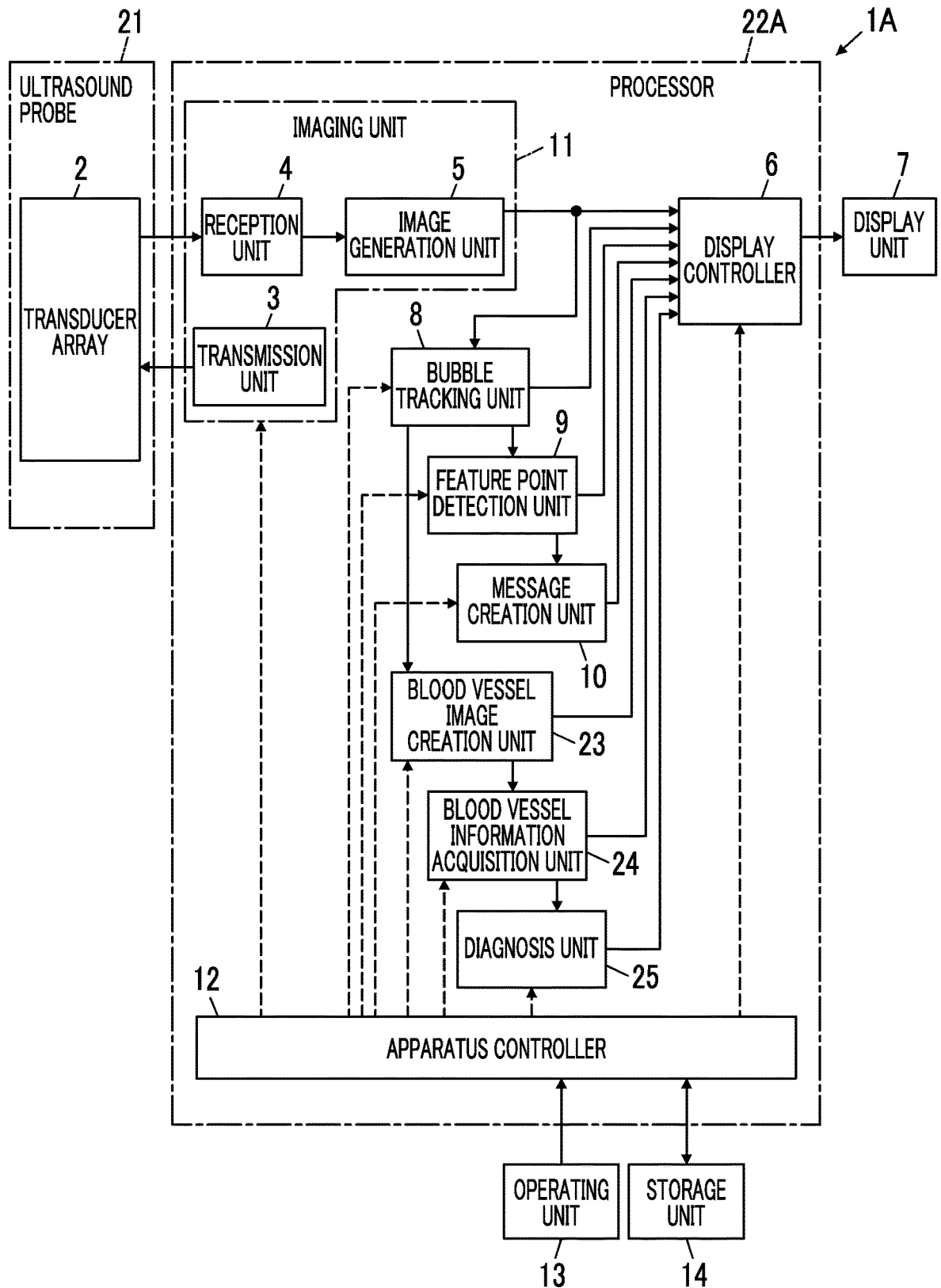
FIG. 8 is a block diagram showing the configuration of an ultrasound diagnosis apparatus according to Embodiment 2 of the invention.

In the ultrasound diagnosis apparatus 1 of Embodiment 1, although the microbubble of the contrast media introduced into the subject is tracked by the bubble tracking unit 8, in an ultrasound diagnosis apparatus 1A of Embodiment 2, a tracking result of the microbubble is analyzed, whereby it is possible to acquire information of a blood vessel through which the microbubble flows. FIG. 8 shows the configuration of the ultrasound diagnosis apparatus 1A of Embodiment 2. In the ultrasound diagnosis apparatus 1A of Embodiment 2, a blood vessel image creation unit 23 is connected to the bubble tracking unit 8, a blood vessel information acquisition unit 24 is connected to the blood vessel image creation unit 23, and a diagnosis unit 25 is connected to the blood vessel information acquisition unit 24. The blood vessel image creation unit 23, the blood vessel information acquisition unit 24, and the diagnosis unit 25 are connected to the display controller 6 and the apparatus controller 12.

The display controller 6, the bubble tracking unit 8, the feature point detection unit 9, the message creation unit 10, the imaging unit 11, the apparatus controller 12, the blood vessel image creation unit 23, the blood vessel information acquisition unit 24, and the diagnosis unit 25 constitute a processor 22A. In this way, the processor 22A in Embodiment 2 is the same as the processor 22 in Embodiment 1, excluding that the blood vessel image creation unit 23, the blood vessel information acquisition unit 24, and the diagnosis unit 25 are included, and the ultrasound diagnosis apparatus 1A of Embodiment 2 has the same configuration as the ultrasound diagnosis apparatus 1 of Embodiment 1 excluding the processor 22A.

The blood vessel image creation unit 23 creates a blood vessel image of the subject based on the trajectory of the microbubble acquired by the bubble tracking unit 8 and displays the created blood vessel image on the display unit 7 through the display controller 6. Here, the created blood vessel image includes information relating to the movement of the microbubble flowing through the blood vessel.

The blood vessel information acquisition unit 24 acquires blood vessel information of the subject from the blood vessel image created by the blood vessel image creation unit 23. Here, the blood vessel information includes at least one of a shape of the blood vessel, a thickness of the blood vessel, the number of blood vessels, and a flow velocity of blood. In acquiring the flow velocity of blood, the blood vessel information acquisition unit 24 analyzes the movement of the microbubble flowing through the blood vessel, in more detail, performs differentiation on each point along the trajectory acquired by the bubble tracking unit 8 using a passing time of the microbubble, thereby being able to calculate the flow velocity of the microbubble and acquire the calculated flow velocity of the microbubble as the flow velocity of blood.

The diagnosis unit 25 performs diagnosis for the blood vessel of the subject based on the blood vessel information acquired by the blood vessel information acquisition unit 24. For example, the diagnosis unit 25 stores a database for diagnosis in advance, collates the blood vessel information with the database, and in a case where a value included in the blood vessel information exceeds a prescribed value, displays a message representing a warning on the display unit 7. Alternatively, for example, the diagnosis unit 25 may collate the blood vessel information with the database and may display a spot, in which a lesion is suspected in the diagnosed blood vessel, on the display unit 7. Furthermore, the diagnosis unit 25 may perform diagnosis for the blood vessel of the subject with reference to a database stored in advance in an external memory (not shown) or the like.

Figure 9:
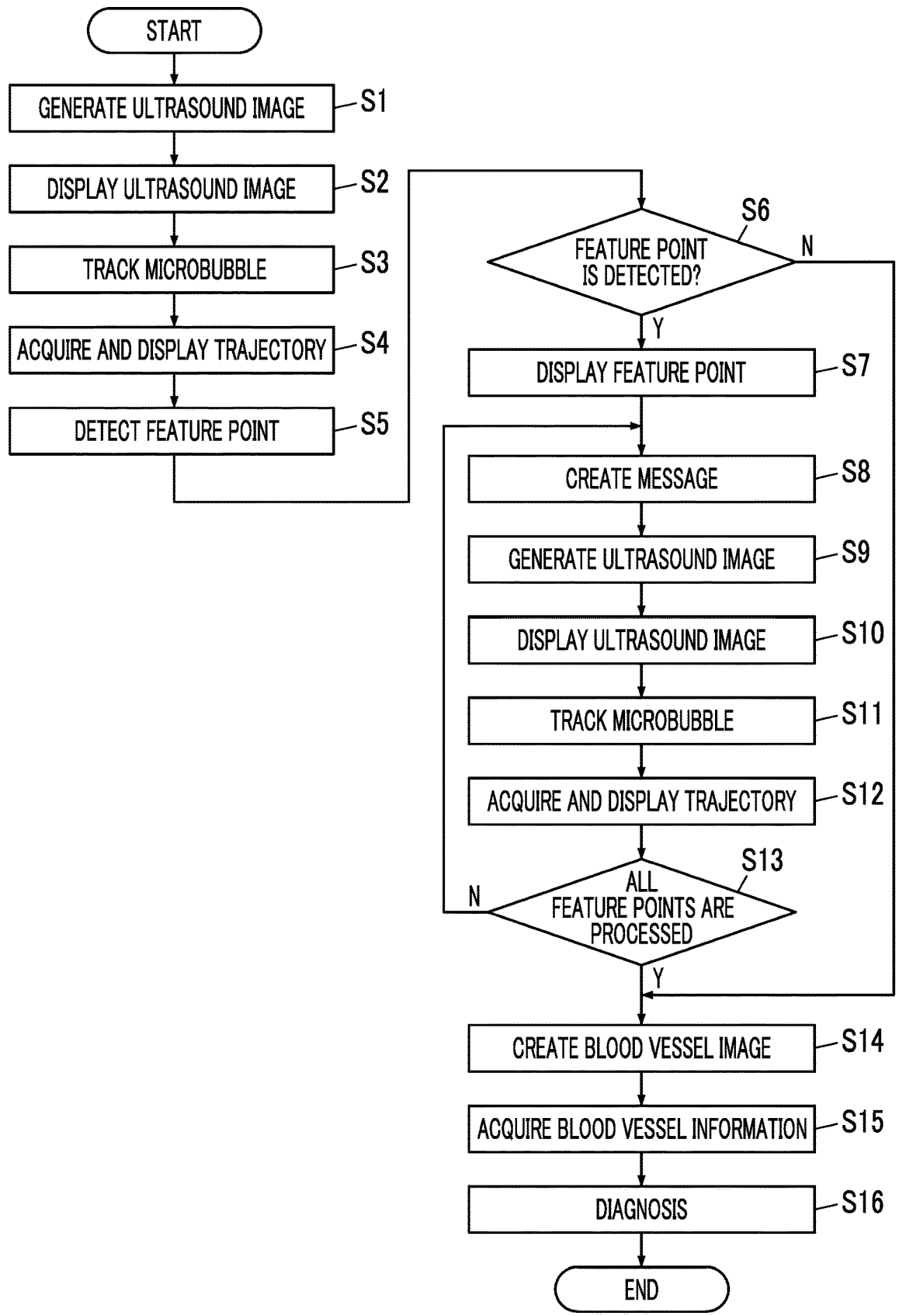
FIG. 9 is a flowchart showing an operation of the ultrasound diagnosis apparatus in Embodiment 2 of the invention.

Next, the operation of the ultrasound diagnosis apparatus 1A in Embodiment 2 will be described in detail referring to a flowchart shown in FIG. 9. Steps S1 to S8 are the same as Steps S1 to S8 in Embodiment 1. The ultrasound diagnosis apparatus 1A performs the generation and the display of the ultrasound image corresponding to one cross section, and performs the acquisition and the display of the trajectory of the microbubble by tracking the microbubble based on the generated ultrasound image. In addition, detection processing of the feature point on the acquired trajectory of the microbubble is performed, and in a case where the feature point is not detected, the process progresses from Step S6 to Step S14. Processing after Step S14 will be described below. In a case where the feature point is detected, the process progresses from Step S6 to Step S7, the detected feature point is displayed on the display unit 7, and the process progresses to Step S8. In Step S8, a message for the user is created such that an ultrasound image corresponding to a cross section different from one cross section corresponding to the ultrasound image generated in Step S1 is obtained.

In a case where the feature point displayed on the display unit 7 and the created message are confirmed by the user, a position of the ultrasound probe 21 is moved by the user such that the ultrasound image corresponding to the cross section different from one cross section corresponding to the ultrasound image generated in Step S1 is obtained. As a result, in Step S9, ultrasound images of a plurality of frames corresponding to a new cross section are generated.

In subsequent Step S10, similarly to Step S2, the ultrasound image generated in Step S9 is displayed on the display unit 7. In Step S11, similarly to Step S3, the bubble tracking unit 8 tracks the microbubble based on the ultrasound images of a plurality of frames generated in Step S9. In Step S12, similarly to Step S4, the bubble tracking unit 8 acquires the trajectory of the microbubble based on a tracking result of the microbubble in Step S11 and displays the acquired trajectory of the microbubble on the display unit 7.

In Step S13, the apparatus controller 12 determines whether or not the processing of Steps S8 to S12 is completed on all feature points to be detected in Step S5. In a case where determination cannot be made that the processing of Steps S8 to S12 is completed on all feature points, that is, in a case where there is a feature point on which the processing of Steps S8 to S12 is not completed, Steps S8 to S13 are repeated until the processing is completed on all feature points. In this case, in Step S8, the message creation unit 10 creates a message corresponding to each feature point by feature point. In this way, as a result of the processing of Steps S8 to S12, in Step S13, in a case where the apparatus controller 12 determines that the processing of Steps S8 to S12 is completed on all feature points, the process progresses to Step S14.

In Step S14, the blood vessel image creation unit 23 acquires a blood vessel image based on the trajectory of the microbubble acquired in Steps S4 and S12. In this case, in a case where the feature point is not detected in Step S5, and the process progresses from Step S6 to Step S14, a blood vessel image extending along only one cross section corresponding to the ultrasound image generated in Step S1 is created. In a case where the feature point is detected in Step S5, and the process progresses from Step S13 to Step S14, blood vessel images are created based on the trajectories of the microbubbles corresponding to a plurality of cross sections.

For example, in a case where the trajectory T1 of the microbubble and the feature point P in one cross section C1 are obtained as shown in FIG. 5, and in addition, the trajectory T2 of the microbubble in the different cross section C2 is obtained as shown in FIG. 7 as a result of tracking the microbubble for the different cross section C2 passing through the feature point P as shown in FIG. 6, the blood vessel image creation unit 23 creates blood vessel images based on the trajectories T1 and T2.

In subsequent Step S15, the blood vessel information acquisition unit 24 acquires blood vessel information based on the blood vessel images created in Step S14. For example, in a case where the blood vessel image creation unit 23 creates the blood vessel images based on the trajectories T1 and T2 of the microbubbles shown in FIGS. 5 to 7, the blood vessel information acquisition unit 24 acquires the blood vessel information based on the blood vessel images corresponding to the trajectories T1 and T2 of the microbubbles.

In Step S16, the diagnosis unit 25 performs diagnosis for the blood vessel of the subject based on the blood vessel information acquired in Step S15 and displays a diagnosis result on the display unit 7. In this way, in a case where the diagnosis of the blood vessel is performed in Step S16, the operation of the ultrasound diagnosis apparatus 1A ends.

As described above, with the ultrasound diagnosis apparatus 1A of Embodiment 2, the blood vessel image is created based on the trajectory of the microbubble acquired by the bubble tracking unit 8 is created, the blood vessel information is acquired, and the diagnosis of the blood vessel is performed. Thus, it is possible to show more information about the blood vessel for the user, and to improve the diagnosis accuracy of the user. In a case where a plurality of feature points are detected, the ultrasound diagnosis apparatus 1A of Embodiment 2 creates a message for the user on all feature points and acquires the trajectory of the microbubble. Thus, it is possible to fully show a position of the blood vessel included in the ultrasound image for the user without depending on the direction of the blood vessel. With this, it is possible to allow the user to easily perform diagnosis based on the ultrasound images corresponding to a plurality of cross sections, and as a result, to improve the diagnosis accuracy of the user.

Figure 10:
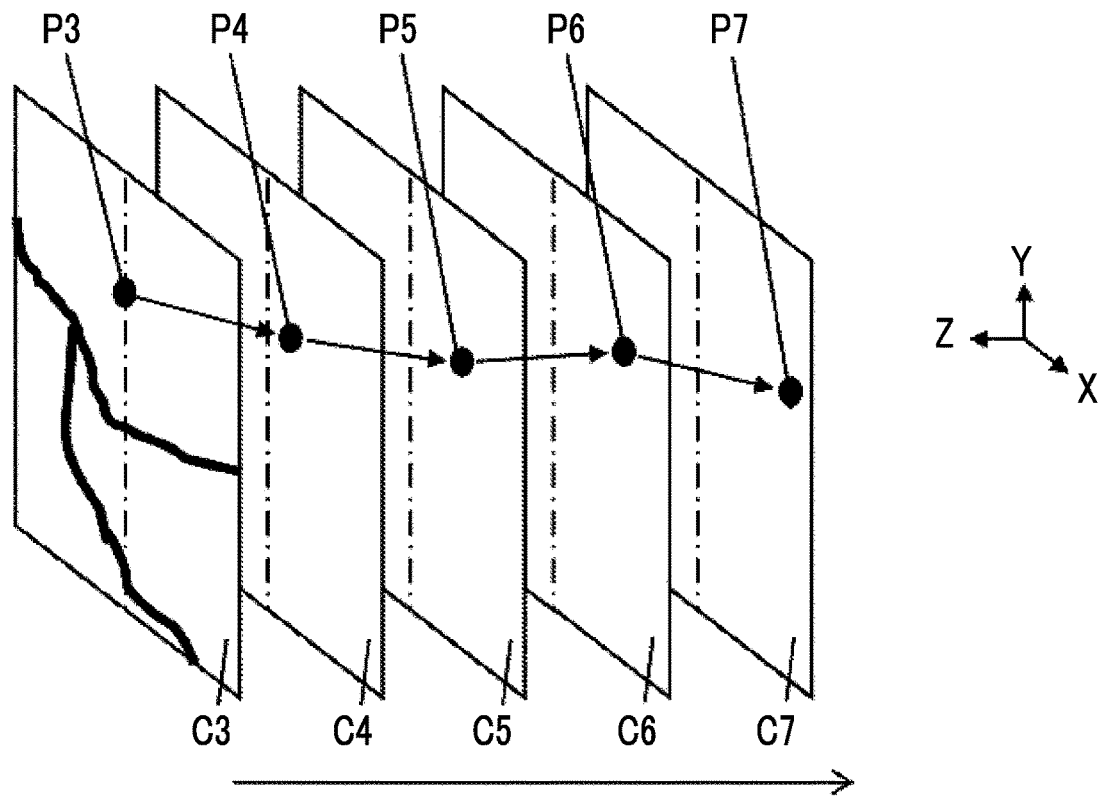
FIG. 10 is a diagram showing an example where a plurality of ultrasound images generated corresponding to a plurality of cross sections parallel to one another are arranged by the ultrasound diagnosis apparatus according to Embodiment 2 of the invention.

In Embodiments 1 and 2, as shown in FIG. 6, although the cross section C2 that intersects one cross section C1 and passes through the feature point P is illustrated as the cross section different from on cross section corresponding to the ultrasound image, in which the feature point is detected, a way of selecting the different cross section is not limited thereto. For example, as shown in FIG. 10, a cross section C4 that is disposed in parallel to one cross section C3, in which a feature point P3 is detected, at a prescribed distance may be set as the different cross section. In this case, for example, the message creation unit 10 can create a message for instructing the user to generate an ultrasound image while moving the ultrasound probe 21 in parallel to one cross section C3 so as to generate an ultrasound image corresponding to the cross section C4. In this case, for example, the message creation unit 10 can create a message for instructing the user to move the ultrasound probe 21 in parallel in a direction toward the periphery of the blood vessel such that the user easily ascertains a manner of bifurcation of the blood vessel.

In this case, for example, the feature point detection unit 9 can detect the feature point P4 based on the ultrasound image corresponding to the cross section C4, and in addition, can detect feature points P5 to P7 based on ultrasound images corresponding to a plurality of cross sections C5 to C7 disposed in parallel to the cross sections C3 and C4 at a prescribed distance, respectively. For example, as shown in FIG. 10, the feature points P3 to P7 detected in this way are superimposed on the ultrasound images corresponding to the cross sections C3 to C7 and are arranged and displayed on the display unit 7, whereby it is possible to show the trajectories of the microbubbles passing through the feature points P3 to P7 for the user.

Figure 11:
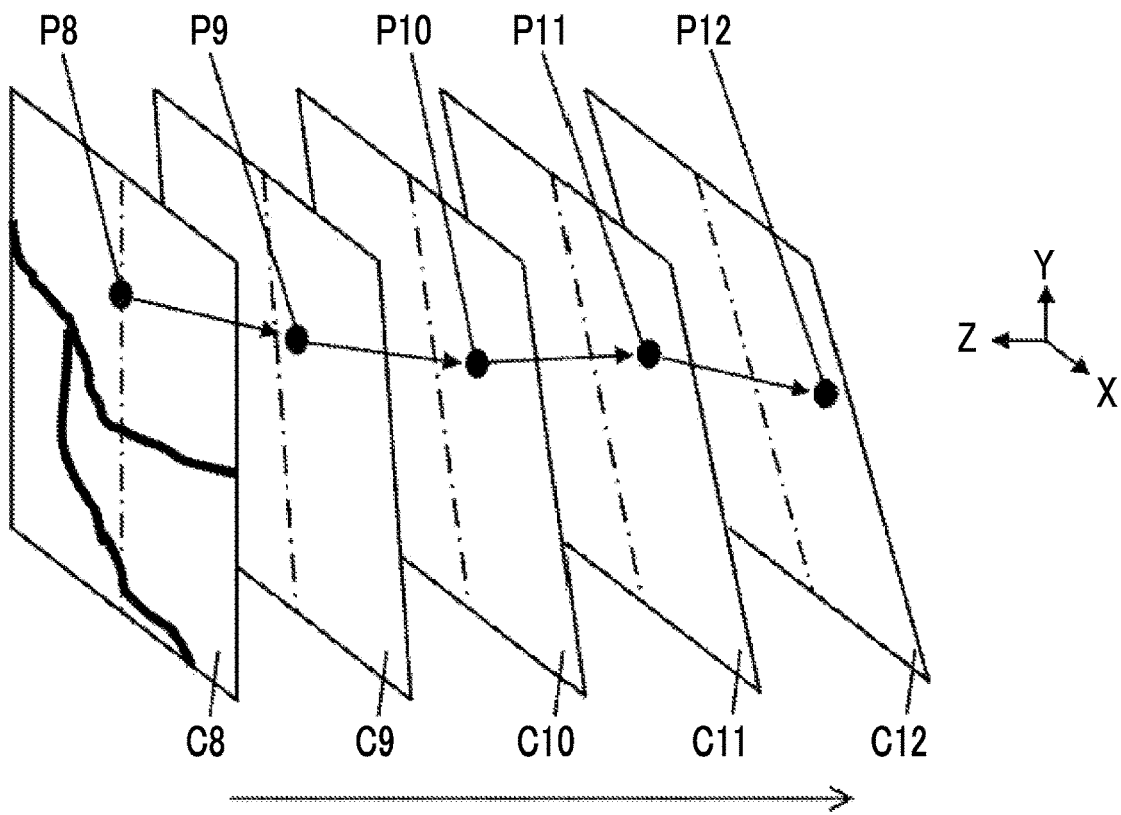
FIG. 11 is a diagram showing an example where a plurality of ultrasound images generated corresponding to a plurality of cross sections having inclination angles different from one another are arranged by the ultrasound diagnosis apparatus according to Embodiment 2 of the invention.

For example, as the ultrasound probe 21, a probe comprising a so-called 1.5-dimensional array, a two-dimensional array, or the like, in which a plurality of ultrasound transducers are arranged in a plurality of columns, can be used. In this case, since scanning with an ultrasonic beam in a three-dimensional manner can be performed using the ultrasound probe 21, it is possible to generate an ultrasound image by electrically inclining a scanning plane little by little in the Z direction while fixing the position of the ultrasound probe 21. In this case, as shown in FIG. 11, it is possible to generate an ultrasound image corresponding to a cross section C9 having an inclination angle from a cross section C8 as a cross section different from one cross section C8, in which a feature point P8 is detected. In this case, for example, the message creation unit 10 can create a message for instructing a user to perform transmission and reception of an ultrasonic beam along a scanning plane having an inclination angle different from the cross section C8 and generating the ultrasound image corresponding to the cross section C9. In this case, for example, the message creation unit 10 can create a message for instructing the user to perform transmission and reception of an ultrasonic beam while increasing the inclination angle of the scanning plane in the direction toward the periphery of the blood vessel such that the user easily ascertains a manner of bifurcation of the blood vessel.

In this case, for example, the feature point detection unit 9 can detect a feature point P9 based on the ultrasound image corresponding to the cross section C9, and in addition, can detect feature points P10 to P12 based on ultrasound images corresponding to different cross sections C10 to C12. For example, as shown in FIG. 11, the feature points P8 to P12 detected in this way are superimposed on ultrasound images corresponding to cross sections C8 to C12 and are arranged and displayed on the display unit 7, whereby it is possible to show the trajectories of the microbubbles passing through the feature points P8 to P12 for the user.

As shown in FIG. 10, in a case where the ultrasound images corresponding to a plurality of cross sections C3 to C7 parallel to one another are obtained, the blood vessel image creation unit 23 can create blood vessel images passing through the feature points P3 to P7 based on coordinate information of the feature points P3 to P7 included in a plurality of cross sections C3 to C7. For example, the blood vessel image creation unit 23 can create the blood vessel images by arranging the ultrasound images corresponding to a plurality of cross sections C3 to C7 at regular intervals and interpolating the coordinate information of the feature points P3 to P7 using regression analysis or the like. Similarly, as shown in FIG. 11, in a case where the ultrasound images corresponding to a plurality of cross sections C8 to C12 are obtained, the blood vessel image creation unit 23 can create the blood vessel images passing through the feature points P8 to P12 based on the coordinate information of the feature points P8 to P12 included in a plurality of cross sections C8 to C12.

Figure 12:
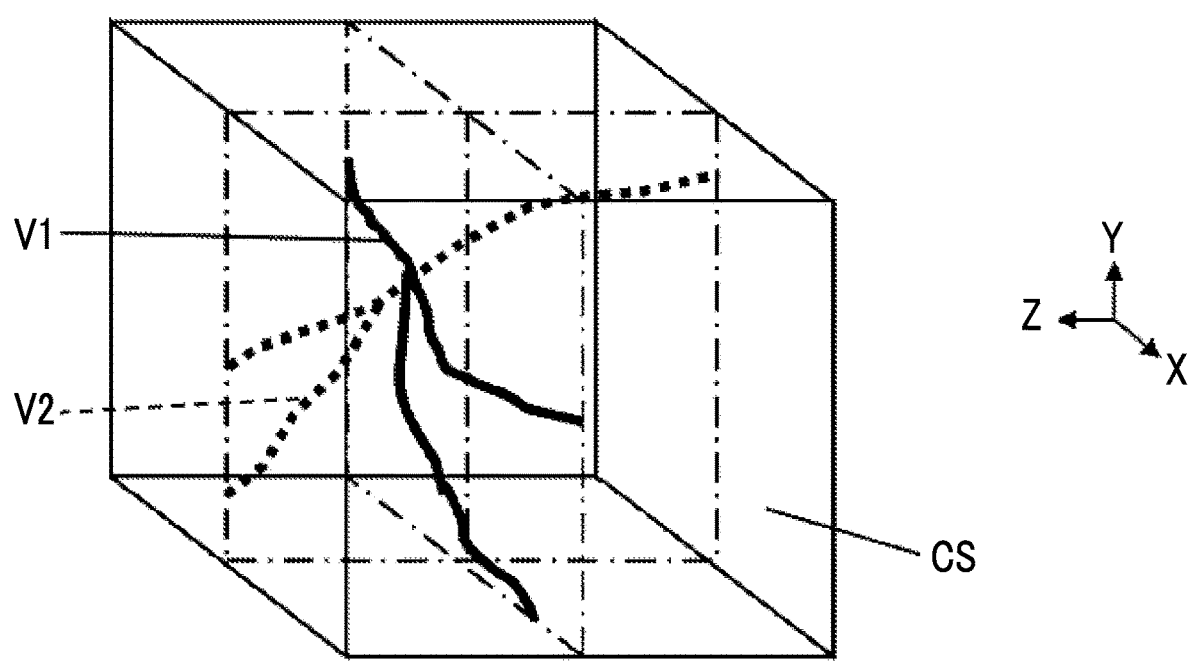
FIG. 12 is a diagram showing a display example of a stereoscopic blood vessel image created by a blood vessel image creation unit in Embodiment 2 of the invention.

As shown in FIG. 12, the blood vessel image creation unit 23 can create a three-dimensional stereoscopic blood vessel image based on the trajectories of the microbubbles acquired by the bubble tracking unit 8 and the feature points detected by the feature point detection unit 9 for the ultrasound images corresponding to a plurality of cross sections and can display the created blood vessel image on the display unit 7. In the example shown in FIG. 12, two blood vessel images V1 and V2 extending along different direction in a three-dimensional coordinate space CS are displayed.

EXPLANATION OF REFERENCES 1, 1A: ultrasound diagnosis apparatus, 2: transducer array, 3: transmission unit, 4: reception unit, 5: image generation unit, 6: display controller, 7: display unit, 8: bubble tracking unit, 9: feature point detection unit, 10: message creation unit, 11: apparatus controller, 13: operating unit, 14: storage unit, 15: amplification unit, 16: AD conversion unit, 17: signal processing unit, 18: DSC, 19: image processing unit, 21: ultrasound probe, 22, 22A: processor, 23: blood vessel image creation unit, 24: blood vessel information acquisition unit, 25: diagnosis unit, C1, C2, C3, C4, C5, C6, C7, C8, C9, C10, C11, C12: cross section, CS: coordinate space, M: message, P, P3, P4, P5, P6, P7, P8, P9, P10, P11, P12: feature point, S: ultrasound image, T1, T2: trajectory of microbubble, V1, V2: blood vessel image

What is claimed is:

1. An ultrasound diagnosis apparatus comprising:
an ultrasound probe having a transducer array; and
a processor configured to:
perform transmission and reception of an ultrasonic beam from the transducer array toward a subject, into which contrast media including microbubbles is introduced;
generate an ultrasound image of the subject from a reception signal outputted by the transducer array;
track movement of the microbubbles based on the ultrasound image corresponding to one cross section of the subject to acquire trajectories of the microbubbles in the one cross section;
detect, as one or more feature points, one or more trajectories, in which a distance between a start point and an end point in a prescribed time range is less than a prescribed value, among the trajectories of the microbubbles; and
display the ultrasound image, the acquired trajectories and the detected one or more feature points on a display,
wherein the processor is further configured to determine the one or more feature points which correspond to one or more cross sections of a blood vessel extending along a direction of penetrating the one cross section vertically or in an inclined manner and create a message instructing a user to obtain one or more additional ultrasound images corresponding to the one or more cross sections of the subject different from the one cross section only in a case where the one or more feature points are detected.

2. The ultrasound diagnosis apparatus according to claim 1,
wherein the one or more cross sections of the subject different from the one cross section are cross sections that are inclined with respect to the one cross section and pass through the one or more feature points.

3. The ultrasound diagnosis apparatus according to claim 2,
wherein, in a case where a plurality of the feature points from the one or more feature points are detected, the processor is further configured to create a message for the user such that ultrasound images corresponding to a plurality of cross sections from the one or more cross sections of the subject different from the one cross section and passing through the respective feature points are obtained.

4. The ultrasound diagnosis apparatus according to claim 3,
wherein the processor is further configured to create the message instructing the user to move a position of the ultrasound probe and obtain the one or more additional ultrasound images.

5. The ultrasound diagnosis apparatus according to claim 3,
wherein the processor is further configured to:
track movement of the microbubbles based on the one or more additional ultrasound images corresponding to the plurality of cross sections from the one or more cross sections of the subject different from the one cross section and passing through the respective feature points to acquire the trajectories of the microbubbles; and
display the acquired trajectories on the display.

6. The ultrasound diagnosis apparatus according to claim 2,
wherein the processor is further configured to create the message instructing the user to move a position of the ultrasound probe and obtain the one or more additional ultrasound images.

7. The ultrasound diagnosis apparatus according to claim 2,
wherein the processor is further configured to:
track movement of the microbubbles based on the one or more additional ultrasound images generated for the one or more cross sections of the subject different from the one cross section to acquire the trajectories of the microbubbles; and
display the acquired trajectories on the display.

8. The ultrasound diagnosis apparatus according to claim 1,
wherein the one or more cross sections of the subject different from the one cross section are a plurality of cross sections parallel to the one cross section.

9. The ultrasound diagnosis apparatus according to claim 8,
wherein the processor is further configured to create the message instructing the user to move a position of the ultrasound probe and obtain the one or more additional ultrasound images.

10. The ultrasound diagnosis apparatus according to claim 8,
wherein the processor is further configured to:
track movement of the microbubbles based on the one or more additional ultrasound images generated for the one or more cross sections of the subject different from the one cross section; and
display the acquired trajectories on the display unit.

11. The ultrasound diagnosis apparatus according to claim 1,
wherein the one or more cross sections of the subject different from the one cross section are a plurality of sections having inclination angles different from one another with respect to the one cross section.

12. The ultrasound diagnosis apparatus according to claim 11,
wherein the ultrasound probe is a probe that is able to perform scanning with the ultrasonic beam from the transducer array in a three-dimensional manner, and
the processor is further configured to create the message to instruct the user to perform transmission and reception of an ultrasonic beam along scanning planes having inclination angles different from one another while fixing a position of the ultrasound probe, and obtain the one or more additional ultrasound images.

13. The ultrasound diagnosis apparatus according to claim 1,
wherein the processor is further configured to:
track movement of the microbubbles based on the one or more additional ultrasound images generated for the one or more cross sections of the subject different from the one cross section to acquire the trajectories of the microbubbles; and
display the acquired trajectories on the display.

14. The ultrasound diagnosis apparatus according to claim 1,
wherein the contrast media is introduced into a blood vessel of the subject, and
the processor is further configured to create a blood vessel image of the subject based on the trajectories of the microbubbles.

15. The ultrasound diagnosis apparatus according to claim 14,
wherein the processor is further configured to acquire blood vessel information of the subject from the blood vessel image.

16. The ultrasound diagnosis apparatus according to claim 15,
wherein the blood vessel information is at least one of a shape of the blood vessel, a thickness of the blood vessel, the number of blood vessels, or a flow velocity of blood.

17. The ultrasound diagnosis apparatus according to claim 15,
wherein the processor is further configured to perform diagnosis of the subject based on the blood vessel information.

18. The ultrasound diagnosis apparatus according to claim 1,
wherein the processor is further configured to perform at least one of changing of color of the one or more detected feature points or marking on the one or more feature points to make the display highlight the one or more feature points.

19. A method of controlling an ultrasound diagnosis apparatus, the method comprising:
performing transmission and reception of an ultrasonic beam toward a subject, into which contrast media including microbubbles is introduced;
generating an ultrasound image of the subject from a reception signal to be output;
tracking movement of the microbubbles based on the ultrasound image generated corresponding to one cross section of the subject to acquire trajectories of the microbubbles in the one cross section;
detecting, as one or more feature points, one or more trajectories, in which a distance between a start point and an end point in a prescribed time range is less than a prescribed value, among the trajectories of the microbubbles; and
displaying the generated ultrasound image, the acquired trajectories and the detected one or more feature points,
the method further comprising:
determining the one or more feature points which correspond to one or more cross sections of a blood vessel extending along a direction of penetrating the one cross section vertically or in an inclined manner and creating a message instructing a user to obtain one or more additional ultrasound images corresponding to the one or more cross sections of the subject different from the one cross section only in a case where the one or more feature points are detected.

* * * * *